United States Patent [19]

Wang et al.

[11] Patent Number: 5,496,546
[45] Date of Patent: Mar. 5, 1996

[54] COMPOSITIONS AND METHODS OF APPLICATION OF REACTIVE ANTIVIRAL POLYADENYLIC ACID DERIVATIVES

[75] Inventors: Jui H. Wang, 477 LeBrun Rd., Amherst, N.Y. 14226; Insug Kang; Mohammed H. Rahman, both of Buffalo, N.Y.

[73] Assignee: Jui H. Wang, Amherst, N.Y.

[21] Appl. No.: 200,650

[22] Filed: Feb. 23, 1994

Related U.S. Application Data

[63] Continuation-in-part of Ser. No. 22,055, Feb. 24, 1993, abandoned.
[51] Int. Cl.$^6$ ............... A61K 31/765; A61K 31/785
[52] U.S. Cl. ............... 424/78.36; 424/78.38; 514/885
[58] Field of Search ............... 424/78.02, 78.36, 424/78.38

[56] References Cited

PUBLICATIONS

Chuan et al Journal of Biological Chem. vol. 263, No. 26 pp. 13003–13006.
Chem. Ab. 77:1242G Steward et al.

Primary Examiner—Peter F. Kulkosky
Attorney, Agent, or Firm—Fliesler, Dubb, Meyer & Lovejoy

[57] ABSTRACT

Novel polyadenylic acid (5') derivatives with 2'-0-(3-fluoro-4,6-dinitrophenyl) groups and/or 2'-0-(2,4-dinitrophenyl) groups have been synthesized and discovered to act as mutation-insensitive and function-specific inhibitors of viral reverse transcriptase. The compositions, preparative procedures and methods of application of these novel compounds for the treatment of humans carrying or infected with AIDS virus and other RNA-viruses, of other mammals carrying RNA-viruses, for the fast but temporary protection of uninfected humans and other mammals against immuno-deficiency viruses and other RNA-virus caused diseases, for the preparation of a formulation containing irreversibly sterilized HIV or other RNA-viruses useful as anti-AIDS and anti-other RNA-virus disease vaccines, for the complete sterilization of possible trace amounts of live HIV and other RNA-viruses in stored transfusion blood, and for the inactivation or removal of trace amounts of ribonuclease in solution and containers used in biotechnology processes have all been disclosed.

18 Claims, No Drawings

COMPOSITIONS AND METHODS OF APPLICATION OF REACTIVE ANTIVIRAL POLYADENYLIC ACID DERIVATIVES

CROSS-REFERENCE

This application is a continuation-in-part of application Ser. No. 08/022,055 filed Feb. 24, 1993, abandoned.

TECHNICAL FIELD

The present invention relates to novel compositions useful for, and methods of, treating diseases, such as AIDS, caused by RNA-viruses. The invention also provides a method of making vaccines against such diseases. Further, the composition is usable to inhibit ribonuclease.

BACKGROUND OF INVENTION

In spite of the worldwide effort, the human immunodeficiency virus (HIV) has until now defeated all attempts to develop an effective anti-AIDS drug or vaccine by resorting to hypermutation tactics. Mutation tactics have likewise until now hampered attempts to develop effective vaccines to other RNA-virus caused diseases such as leukemia and influenza.

One of the strategies for combating RNA-viruses such as the HIV AIDS (acquired immunodeficiency syndrome) virus is to inactivate the reverse transcriptase of HIV (HIV RT). Unfortunately, the unusually high mutation rate of the virus has hitherto prevented the development of an effective anti-HIV drug or vaccine. The hypermutable HIV can develop resistance rapidly toward all known inhibitors of small molecular weight ($M_r$<1000 dalton) such as AZT, ddC, ddI and nevirapine [Larder, et al., Science 243, 1731 (1989); Larder and Kemp, Science 246, 1155 (1989); St. Clair, et al., Science 253, 1557 (1991); Shih, et al., Proc. Natl. Acad. Sci. USA 88, 9878 (1991)].

It is known (Chuan and Wang, J. Biol. Chem. 263, 13003 (1981)) that the affinity reagents 3'-O-( 5-fluoro-2,4-dinitrophenyl) ADP ether and 3'-O-(5 -fluoro-2,4-dinitrophenyl) ATP ether are capable of labelling the active site of mitochondrial $F_1$-ATPase and of inhibiting the ATPase. However, 3'-O-(5 -fluoro-2,4-dinitrophenyl) ADP ether and the corresponding ATP ether require a million-fold higher molar concentration to inhibit the reverse transcriptase of HIV (HIV RT), nor can they inhibit HIV RT or other RNA-viruses in a manner which is mutation-insensitive.

It is also known (Fukui and De Clercq, Biochem J 203, 755–760 and Shannon, Ann. N.Y. Acad. Sci. 284, 472–507) that anti-viral compounds such as poly(2-fluoroadenylic acid), poly(2-bromoadenylic acid), poly(2-iodoadenylic acid) and 1-(4-fluorobenzyloxy) adenosine polyadenylic acid, inhibit reverse transcriptase. All of these compounds are derivatized by attaching halogen atoms or other groups to the adenine residues in the polymers. The best of these compounds is $(fl^2A)_n$ which inhibited murine leukemia RT with an $IC_{50}$ of 0.04 μg/ml. The FDNP-poly[A] of the present invention inhibited the same RT with an $IC_{50}$ of 0.0017 μg/ml (at a 23-fold lower concentration).

DISCLOSURE OF INVENTION

In accordance with an embodiment of the invention a composition of matter is set forth. The composition comprises Y-poly[A] representable by the formula:

$$M_n(Y)_m X_i [A]_n$$

where:
$[A]_n$=polyadenylic acid (5') with n adenylic acid residues,
Y=FDNP, DNP, or partially FDNP and partially DNP,
FDNP=3-fluoro-4,6-dinitrophenyl groups, attached covalently to m of the n 2'-OH groups of $[A]_n$ via ether linkage,
DNP=2,4-dinitrophenyl groups, attached covalently to m of the n 2'-OH groups of $[A]_n$ via ether linkage,
X=an acyl group,
i=0 or 1,
M=a cation selected to provide a desired degree of solubility for the composition,
and has one of the generic structures:

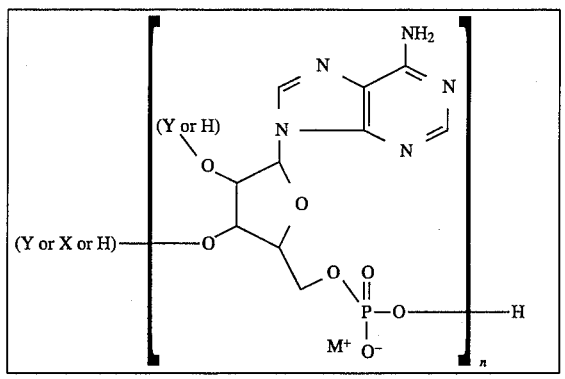

or

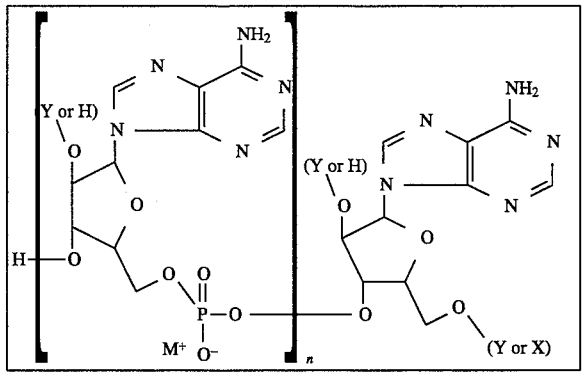

and having a ratio of Y groups to adenine units of at least about 1:5 and wherein n is sufficiently large so that the Y-poly[A] can substantially completely fill the active site cleft of an RNA-virus RT to effectively inactivate reverse transcriptase and/or can effectively inactivate ribonuclease.

Another embodiment of the invention comprises a method of treating a mammal having a disease caused by an RNA-virus. The method comprises the administration to the mammal of an effective treatment amount of Y-poly[A].

Still another embodiment of the invention is a method of temporarily protecting a healthy mammal from an RNA-virus infection. The method comprises administering to the mammal an effective preventative amount of Y-poly[A].

Another embodiment yet of the invention comprises methods of preparing anti-RNA-virus vaccines and of vaccinating to provide protection against an RNA-virus caused disease. The method comprises introducing to a patient an antigen comprising an RNA-virus which has been irreversibly inactivated by Y-poly[A] wherein Y is at least partially FDNP, whereby the patient produces one or more antibodies to the antigen, the antibodies to the antigen also comprising antibodies to the RNA-virus.

A further embodiment still of the invention comprises a method of sterilizing an RNA-virus in blood aliquots intended for transfusion. The method comprises adding to the blood aliquots an effective amount for sterilization of Y-poly[A] wherein Y is at least partially FDNP.

One more embodiment of the invention comprises a method of removing ribonuclease from a solution comprising passing the solution through an affinity column containing immobilized FDNP-poly[A] or DNP-poly[A].

Ribonuclease can also be irreversibly inhibited by adding an effective amount of Y-poly[A], wherein Y is at least partially FDNP, to a solution of the ribonuclease.

Another useful method in accordance with an embodiment of the invention is to irreversibly inactivating an RNA-virus. The method comprises contacting the RNA-virus with an effective amount for inactivating the RNA-virus of FDNP-poly[A].

BEST MODE FOR CARRYING OUT INVENTION

A new type of polymeric inhibitor is set forth herein that binds tightly to and substantially completely fills the long binding cleft at the active site of HIV reverse transcriptase (HIV RT). The new inhibitors were synthesized and were discovered to inactivate HIV RT in solution rapidly, and in the case of the Y-poly[A] having at least a portion of the Y being FDNP irreversibly, and to enable susceptible lymphocytes to continue their normal growth after the addition of live HIV to the culture plate. The inhibitors have DNP- and/or FDNP- groups covalently attached to the ribose residues in the polymer. These inhibitors are function-specific and hence have low toxicity, but are not species-specific and hence are indicated to be mutation-insensitive. The compositions and methods of using these novel compounds in five different pharmaceutical and biotechnological applications are disclosed. A group of mutation-insensitive inhibitors has been developed based on the following rationale.

Recent crystallographic studies show that the polymerase site in HIV RT consists of an open-ended cleft that is long enough to accommodate a segment of RNA 25 to 30 residues in length []K<i, et al., *Science* 256, 1783 (1992); Arnold, et al., *Nature* 357, 85 (1992). Presumably, this active site cleft binds polyadenylic acid (5') (hereinafter referred to as "poly [A]") preferentially, because the complex poly[A]-[dT]$_{12}$ has been used successfully and quite often as template-promoter in in vitro reverse transcription experiments. Therefore, hydrophobic groups were attached to poly[A] at its 2'-OH positions to improve the binding affinity to RT without hindering its template function. The resulting poly [A] derivative has the capability of binding to HIV RT by substantially completely filling its active site cleft and acts as a multifunctional affinity reagent.

In view of the long-standing practice of labelling nucleophilic groups of proteins with Sanger's reagent 1-fluoro-2, 4-dinitrobenzene, electrophilic 3-fluoro-4,6-dinitrophenyl (FDNP) groups were attached to poly[A] at its 2'-OH positions through ether linkages by a previously published procedure for mononucleotides [Chuan and Wang, *J. Biol. Chem*, 263, 13003 (1981), the disclosure of which is incorporated herein by reference]. These electrophilic FDNP groups serve to irreversibly react with and to bind to nucleophilic groups in the active site cleft thus blocking the action of reverse transcriptase. The structure of the resulting polymer derivative, designated as FDNP-poly[A], is represented by a structure shown below with general formula:

$$M_n(FDNP)_m X_i[A]_n$$

where:

[A]$_n$=polyadenylic acid (5') with n adenylic acid residues,

FDNP=3-fluoro-4,6-dinitrophenyl groups, attached covalently to m of the n 2'-OH groups of [A]$_n$ via ether linkage, X=an acyl group, i=0 or 1, M=a cation selected to provide a desired degree of solubility for the composition, and has one of the generic structures:

or

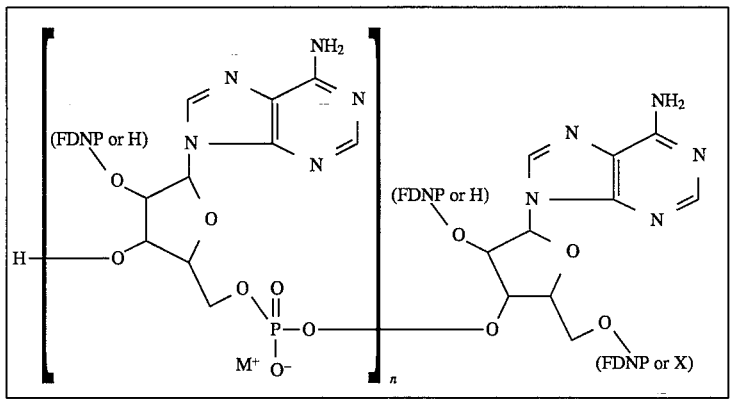

It was further discovered that DNP-poly[A] is also effective in inactivating reverse transcriptases and ribonucleases. Indeed, while the action of DNP-poly[A] is not irreversible it was found that with 1 DNP-group per 1.5 adenine residues, the latter is about twelve times as effective (i.e., is equally effective at one-twelfth the dosage) as is FDNP-poly[A]. The polymer derivative, designated as DNP-poly[A], is represented by a structure shown below with general formula:

$$M_n(DNP)_m X_i[A]_n$$

where:

[A]$_n$ =polyadenylic acid (5') with n adenylic acid residues,

DNP=2,4-dinitrophenyl groups, attached covalently to m of the n 2'-OH groups of [A]$_n$ via ether linkage, X=an acyl group, i=0 or 1, M=a cation selected to provide a desired degree of solubility for the composition, and has one of the generic structures:

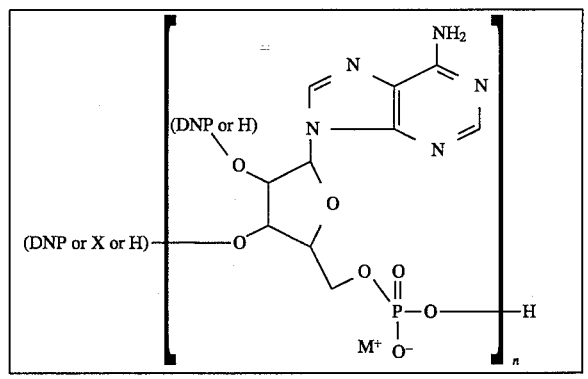

or

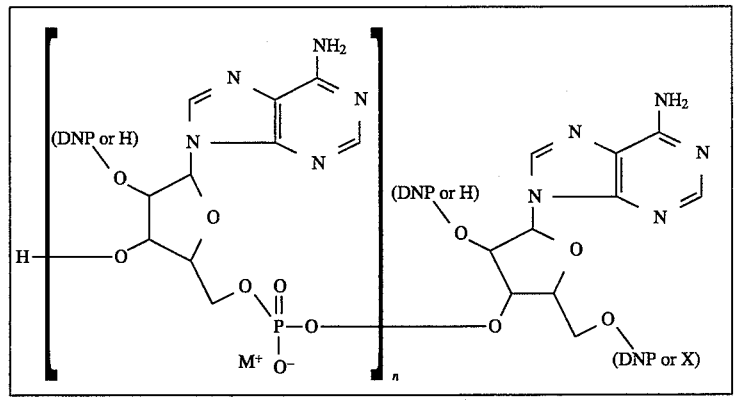

In both cases, n is sufficiently large so that the Y-poly[A] (where Y=DNP, FDNP or where some Y are DNP and others are FDNP) substantially completely fills the active site cleft of the RNA-virus RT to effectively inactivate the reverse transcriptase and/or can effectively inactivate ribonuclease. Generally it is preferred that n be relatively large, suitably 20 or greater and preferably 25 or greater. Actual experiments are set forth below for a relatively higher molecular weight Y-poly[A](h-$M_r$), n≈270, m≈69, $M_r$≈1.1×10$^5$ (where $M_r$ represents molecular weight) and for a relatively lower molecular weight Y-poly[A](l-$M_r$), n≈28, m≈9, $M_r$≈1.2×10$^4$.

FDNP groups are generally attachable to the poly[A] to provide a ratio of FDNP group to [A] of no more than about 1:4. DNP groups are attachable to the poly[A] to provide a considerably higher ratio of about 1:1.5. Mixed FDNP/DNP poly[A] polymers can also be formed. Generally, 1,3-difluoro-2,4-dinitrobenzene (DFDB) will first be reacted with the poly[A] to provide a ratio of FDNP to [A] of from about 1:4 to about 1:10. Then, the product will be reacted with 1-fluoro-2,4-dinitrobenzene (FDNB) so that the resulting composition will have an overall ratio of FDNP plus DNP groups to [A] which is as high as can be attained, generally of greater than 1:4, preferably greater than 1:2.

The cation, M, can be any cation which will provide a sufficient concentration of the composition to accomplish a desired purpose, e.g., inactivate ribonuclease, treat a disease caused by and RNA-virus, produce inactivated (dead) virus for vaccination, sterilize stored blood, etc. The potassium salt was used in the experiments reported herein but, for example, the ammonium, rubidium, cesium or other salt can be utilized in its place.

An important factor is the molar ratio of Y groups to [A] (adenine) units. In general, the effectiveness of the individual Y-poly[A] compound increases with increased Y to [A] molar ratio. Accordingly, it is desirable that this ratio be relatively high. Generally, this ratio should be at least about 1:10 with higher ratios, for example 1:5 and above being preferred. The experiments reported herein were carried out with Y-poly[A] compounds having 1:1.5, 1:3.9 and 1:4.8 ratios. Even higher ratios should be desirable.

We have discovered that at nanomolar concentrations, Y-poly[A] is an effective inhibitor of reverse transcriptases and therefore appears to be an effective anti-RNA-virus treatment (and is also an effective and, when Y is at least partially FDNP, irreversible inhibitor of ribonuclease), but that even at micromolar concentrations it does not inhibit the essential host cell enzymes that were tested in vitro, including RNA-polymerase II, cAMP-dependent protein kinase, pyruvate kinase, hexokinase and adenylate kinase. Thus, dosages can be formulated which are effective for irreversibly inhibiting reverse transcriptase in the RNA-viruses but which do not inhibit essential cell enzymes. The association of Y-poly[A] with ribonuclease can be used to inactivate and/or remove ribonuclease from solution. For example, Y-poly[A] wherein at least a portion of Y is FDNP can be added to a solution of ribonuclease to irreversibly inhibit the ribonuclease. Alternatively and preferably, the Y-poly[A] can be associated with an affinity material, generally with an affinity column, and a solution containing ribonuclease can be passed through the column. The ribonuclease is then held on the column and the solution exiting from the column can be made ribonuclease free. It is preferable when using the column technique that the Y-poly[A] be DNP-poly[A] since the FDNP group of FDNP-poly[A] can be hydrolyzed on the column, whereas a DNP-poly[A] column can be washed and used again. The column material used is not critical. It can be substantially any column material with which the Y-poly[A] can be associated. For example, we have used a cellulose column.

A long inhibitor molecule such as Y-poly[A] with multiple points of covalent attachment of FDNP groups or non-covalent attachment of DNP groups to many specific amino acid residues at the active site of HIV RT was selected to be a probably mutation-insensitive inhibitor, because it is highly improbable for all these specific amino acid residues to be altered by a single set of random mutations so that the mutant enzyme would no longer be able to bind Y-poly[A] but would still bind the template poly[A]. In order to stay viable, the hypermutable HIV must have a RT that maintains a long active site cleft. It would be very difficult for the viable mutant HIV RT to avoid the binding of such an inhibitor molecule. This inference was confirmed by the observation that in spite of the substantial differences between the primary structures of HIV RT, avian myeloblastosis virus RT (AMV RT) and Moloney murine leukemia virus RT (MLV RT), all three reverse transcriptases were inactivated in 10 minutes or less at 25° C. by nanomolar concentrations of FDNP-poly[A].

Y-poly[A](h-$M_r$) and Y-poly[A](l-$M_r$) were tested at our request as potential anti-HIV drugs in vitro with susceptible lymphocytes in the presence of by the Developmental Therapeutics Program of the Division of Cancer Treatment in The National Cancer Institute, (NCI). These reactive polymers were found to be effective in keeping the lymphocytes viable in the presence of HIV (see Example 5 below).

Since these polymers were designed to inactivate all reverse transcriptases, they can also be utilized for treating other diseases caused by RNA-viruses, e.g., adult T-cell leukemia/lymphoma, hepatitis A, C, D and E, influenza, parainfluenza, infant bronchiolitis and pneumonia, common cold, measles, mumps, etc. Thus, diseases caused by, by way of non-limiting example, the RNA-viruses HTLV (adult T-cell leukemia/lymphoma virus), HAV (Hepatitis A virus), HAC (Hepatitis C virus), HDV (Hepatitis D virus), HAC (Hepatitis E virus), HEV (influenza virus), parainfluenza virus, RSV (respiratory syncytial virus), common cold causing coronavirus and rhinovirus, measles virus and mumps virus can be controlled by use of the present invention. Other RNA-virus caused diseases can likewise be controlled by use of the present invention.

The invention will be better understood by reference to the following examples.

EXAMPLE 1

Preparation of Y-poly[A](h-$M_r$)

Procedure 1

Ten milligrams of the potassium salt of Poly[A] (obtained from Sigma, $M_r$~1.1×10$^5$) were dissolved in 0.5 mL water and 1.6 mL of 0.2M $K_2CO_3$+ 1.5M $KHCO_3$ solution (pH 9.2). The stirred solution was mixed with 0.80 mL of an acetone solution containing a tenfold excess of 1,3-difluoro-2,4-dinitrobenzene (DFDB) which was added in three equal aliquots at 12-hour intervals. After the reaction had progressed for 48 hours at room temperature, the excess DFDB was removed by repeated extraction with a 7:1 (v/v) mixture of methylene chloride and dimethylsulfoxide. The resulting aqueous solution was centrifugally gel-filtered through Sephadex G-25-80 and subsequently lyophilized. The molar ratio of 3-fluoro-4,6-dinitrophenyl to adenine groups in the product was calculated from the observed absorbance at 330 and 259 nm respectively to be 1/3.9, using 3-fluoro-4,6-dinitrophenyl ethyl ether ($\epsilon_{259}$=3900, $\epsilon_{330}$=6300) and AMP ($\epsilon_{259}$=15400) as the standards. Thus the average polymeric inhibitor had 270 adenine residues and 69 2'-O-FDNP groups per molecule. The absorbance of a dilute solution of the FDNP-poly[A](h-$M_r$) did not decrease significantly (<5%) after its pH was lowered from 9 to 5. This observation shows that the fraction of 3-fluoro-4,6-dinitrophenyl groups in the product which had been hydrolyzed to the nonreactive 3-hydroxy-4,6-dinitrophenyl groups during the preparation was less than 5%. Yield of product=3 mg.

Procedure 2

Ten milligrams of the potassium salt of Poly[A] (obtained from Sigma, $M_r\sim 1.1\times 10^2$) were dissolved in 0.5 mL water and 0.1 mL of 0.1M $K_2CO_3$+ 2.0M $KHCO_3$ solution (pH 8.8). The stirred solution was mixed with 0.4 mL of an acetone solution containing a five-fold excess of 1,3-difluoro-2,4-dinitrobenzene (DFDB) which was added in four aliquots at 6-hour intervals. During the reaction the pH of the reaction mixture was checked and readjusted to 8.8 by adding $K_2CO_3$ and $KHCO_3$. The progress of the reaction was monitored by TLC analysis of the reaction mixture as a function of time on a Kodak Cellulose Plate with fluorescent indicator, using (20 mM $K_2HPO_4$+20 mM $KH_2PO_4$): $CH_3CN$=2:1 (v/v) as the developing solvent. Eventually all of a band at $R_f$=0.38 from poly A faded and a new FDNP-poly A band at $R_f$=0.77 grew in intensity. After the reaction had progressed until the band at $R_f$=0.38 had disappeared, usually after about 24 hours at room temperature, the excess DFDB was removed by repeated extraction with a 7:1 (v/v) mixture of methylene chloride and dimethyl sulfoxide. The resulting aqueous solution was centrifugally gel-filtered through Sephadex G-50-80 or dialyzed and subsequently lyophilized. The molar ratio of 3-fluoro-4,6-dinitrophenyl to adenine groups in the product was calculated from the observed absorbance at 330 and 259 nm respectively to be 1/4.8, using 3-fluoro-4,6-dinitrophenyl ethyl ether ($\epsilon_{259}$=3900, $\epsilon_{330}$=6300) and AMP ($\epsilon_{259}$=15400) as the standards. The FDNP/adenine ratio of 1/4.8 was confirmed by $^{19}$F-NMR and by $^{31}$P-NMR.

While Procedure 1 yielded a product having a desirably higher ratio than did Procedure 2 of FDNP groups to adenine groups it was found that after the 48 hour reaction time about 5% of the 5-fluoro groups had hydrolyzed into OH groups. Hydrolysis was not found to have occurred when the reaction time was limited to 24 hours. The hydrolyzed material was not separable from the product. Accordingly, Procedure 2 is preferred.

DNP-poly A was synthesized similarly to Procedure 2 with 1-fluoro-2,4-dinitrobenzene (FDNB) replacing DFDB. In the synthesis of DNP-poly A, poly A was allowed to react with excess FDNB for 48 hours at room temperature, and the DNP-group to adenine residue molar ratio in the product DNP-poly A was 1/1.5. This ratio was higher than that obtained with the FDNP-poly[A] since in that instance the reaction was terminated after 48 hours to avoid appreciable hydrolysis of the 5-fluoro group.

EXAMPLE 2

Preparation of FDNP-poly[A](l-$M_r$)

A mixture of ADP and AMP at 28:1 molar ratio was prepared by dissolving 867 mg ADP (K-salt), 25 mg AMP (free acid) and 393 mg $K_2CO_3$ in 4 mL water. Its pH was changed from 8.2 to 9.05 by successive additions of solid $K_2CO_3$. The solution was then mixed with 20 µL of 1M $MgCl_2$ and 8 units of polynucleotide phosphorylase (obtained from Sigma; derived from *E. coli*). After the reaction mixture was incubated at 37° C. for 48 hours, it was centrifugally gel-filtered through Sephadex G-25-80 to remove all ADP, AMP and oligonucleotides of molecular weight below 5000. Measurement of absorbance at 259 nm showed that the filtrate contained 63 mg of product FDNP-poly[A](l-$M_r$). A second gel-filtration of an aliquot of this FDNP-poly[A](l-$M_r$) solution through Sephadex G-50-80 showed that 99.7% of the oligomers made this way have $M_r$<10000. This FDNP-[A]poly(l-$M_r$) was subsequently used to react with FDNB in a similar way as described above to form FDNP-poly[A](l-$M_r$). Molar ratios of FDNP-groups/adenine residues=1/3.9.

FDNP-poly[A](l-$M_r$) was also synthesized following Procedure 2 above and yielded a product having an FDNP/adenine molar ratio of 1/4.8. DNP-[ A]poly(l-$M_r$) was prepared similarly and had a DNP/adenine molar ratio of 1/1.5.

EXAMPLE 3

Irreversible Inhibition of Viral Reverse Transcriptases in Solution by FDNP-poly[A]

Reverse transcriptase samples from HIV (HIV RT) and from Moloney murine leukemia virus (MLV RT) and from avian myeloblastosis virus (AMV RT) were separately incubated with FDNP-poly[A] at 25° C. in a Tris-HCl buffer (0.1M, pH 8.2) containing 1 mM $MgCl_2$ and 125 mM KCl and measured for RT activity. In each experiment, the selected enzyme was incubated for 10 minutes at 25° C. in an incubation mixture containing the potassium salt of the inhibitor at a given concentration. After ten minutes the incubated mixture was rapidly injected into an assay solution and further incubated for 10 min at 37° C., then precipitated with trichloroacetic acid, washed, and assayed for the radioactive polynucleotide formed by scintillation counting. The assay mixture contained 125 mM Tris-HCl (pH 8.2), 1 mM $MgCl_2$, 125 mM KCl, 250 µM [$^3$H]dTTP as the substrate and 23 nM Poly[A]-[dT]$_{12}$ as the template.

For each reverse transcriptase the observed percentage of enzyme activity left after 10 minutes preincubation with FDNP-poly[A] at 25° C. was plotted as a function of inhibitor concentration, and the concentration of the inhibitor required for 50% inhibition of the enzyme ($IC_{50}$) was determined from the graph. The results are summarized below. Similar results were obtained with DNP-poly[A].

| Enzyme | Inhibitor | $IC_{50}$ (nM) |
| --- | --- | --- |
| HIV RT | FDNP-poly[A] (h-$M_r$) | 6 pM |
| HIV RT | FDNP-poly[A] (l-$M_r$) | 400 nM |
| MLV RT | FDNP-poly[A] (h-$M_r$) | 15 pM |
| AMV RT | FDNP-poly[A] (h-$M_r$) | 12 pM |

The observed $IC_{50}$ values show that DNP-poly [A](h-$M_r$), and FDNP-poly [A](h-$M_r$) and FDNP-poly [A](l-$M_r$) are powerful inhibitors of reverse transcriptase in aqueous solution. Kinetic measurements indicated that both DNP-poly [A] and FDNP-poly[A] compete with the template-primer polyadenylic acid-dodecathymidytic acid (poly[A]-[ dT]$_{12}$) for the same binding site in the HIV RT molecule. Loading the incubated mixture onto a cellulose-oligo[dt] column and subsequent separation by elution chromatography showed that FDNP-poly[A] binds to reverse transcriptase covalently. Therefore its inactivation of the enzyme is irreversible.

The above data also show that in spite of their substantial differences in primary structure, the three viral reverse transcriptases, HIV RT, MLV RT and AMV RT were all inactivated in ten minutes at 25° C. by subnanomolar concentrations of FDNP-poly[A]. This is a strong indication that FDNP-poly[A] is mutation-insensitive.

EXAMPLE 4

Inhibition of Different HIV Reverse Transcriptases DNP-poly[A] and FDNP-poly[A]

The inhibition of different mutant HIV RT's by DNP-poly[A] and FDNP-poly[A] was kindly measured gratis by Dr. Joe C. Wu with the RT from four different strains of the human virus: HIV-1 RT (wild type), HIV-2 (wild type), HIV-1$_{41,215}$ RT (AZT-resistant mutant, Thr 215→Tyr, Met 41→Leu), HIV-1$_{181c}$ RT (Nevirapine-resistant mutant), using poly C-[dG]$_{12-18}$ as the template and [$^3$H]dGTP as the substrate. The assay conditions are the same as in Example 3. The observed approximate IC$_{50}$ values are summarized in the Table below:

| | IC$_{50}$ of the RT (nM) | | | |
|---|---|---|---|---|
| Inhibitor | HIV-1 (wild) | HIV-2 (wild) | HIV-1$_{41,215}$ | HIV-1$_{181C}$ |
| DNP-poly[A] | 3.8 ± 0.5 | 1.6 ± 0.2 | 2.2 ± 0.3 | 0.34 ± 0.07 |
| Poly[A] | — | — | — | — |
| FDNP-poly[A] | 1.5 ± 0.6 | 1.1 ± 0.2 | 1.2 ± 0.3 | 0.65 ± 0.11 |

It was found in these experiments that both DNP-poly[A] and FDNP-poly[A] are potent inhibitors of all four reverse transcriptases but that poly[A] itself has no inhibitory effect.

EXAMPLE 5

Protection of Susceptible Lymphocytes from HIV by DNP- and FDNP-poly[A](h-M$_r$) and by FDNP-poly[A](l-M$_r$)

FDNP-poly[A](h-M$_r$), DNP-poly[A](h-M$_r$) and FDNP-poly[A](l-M$_r$) were tested as potential anti-AIDS drugs in vitro with susceptible lymphocytes in the presence of HIV by the Developmental Therapeutics Program of Division of Cancer Treatment in the National Cancer Institute (NCI). All three inhibitors were confirmed as being active. The NCI protocol involves mixing various concentrations of FDNP-poly[A](h-M$_r$), DNP-poly[A](h-M$_r$) or FDNP-poly[ A](l-M$_r$) and susceptible T4 lymphocytes (CEM-SS cell line) with or without HIV in microculture plates, incubating the plates for six days, then determining the number of remaining viable cells using a colorimetric endpoint [method described in Weislow, et al., *J. Natl. Cancer Inst.* 81, 577–586 (1989)].

The test results show that FDNP-poly[A] and DNP-poly [A] are both effective in keeping the lymphocytes viable in the presence of HIV. The observed effective concentrations (EC$_{50}$) are 2.65± 0.15 µg/mL or 24±2 nM for FDNP-poly [A](h-M$_r$) and 0.2± 0.1 µg/mL or 2±1 nM for DNP-poly[A] [h-M$_r$]). Therefore these polymers are potent antiviral agents. The soluble salt of either polymer can be used directly to treat mammals infected by HIV either in an appropriate solution for parenteral administration or in the form of pellets to be taken orally.

EXAMPLE 6

Stability of Y-poly[A](h-M$_r$) in 0.01M Hydrochloric Acid and in the Presence of Pepsin at 37° C.

Human stomach juice contains pepsin and approximately 0.01M HCl. To simulate the acid conditions inside human stomach, we incubated FDNP-poly[A] in 0.01M HCl at 37° C., and found that its potency as an irreversible inhibitor of HIV RT decreased only 50% after 4 hours of incubation in 0.01M HCl. DNP-poly[A] was found to be even more stable under the same conditions. The results for FDNP-poly[A] appear in the following table.

| Incubation at 37° C. (h) | 0 | 1/2 | 1 | 2 | 4 |
|---|---|---|---|---|---|
| IC$_{50}$ (nM) | 27 | 22 | 22 | 21 | 34 |

In a separate experiment, FDNP-poly[A](h-M$_r$) (34 nM) was incubated at 37° C. in a 0.01M HCl solution containing 1.0 mg/ml of pepsin. It was found that the potency of the inhibitor was unaffected after 2 hours but decreased to 65% after 4 hours of incubation. These observations suggest that the potency of FDNP-poly[A] against HIV will not be destroyed by stomach juice in 2 hours. Consequently, the solid salt of FDNP-poly[A] may be mixed with proper filler and pressed into pellets or packed in capsules for oral administration.

EXAMPLE 7

Stability of FDNP-poly[A] in Human Blood Serum at 37° C.

A frozen sample of normal human serum (Male, Type AB, from Sigma) was thawed and used to dissolve FDNP-poly [A](h-M$_r$) (34 nM). The relative potency of this inhibitor of HIV RT was determined as a function of incubation time at 37° C. and listed below:

| Incubation time (h) | 0 | 0.5 | 1.0 | 2.0 | 4.0 |
|---|---|---|---|---|---|
| Relative potency (%) | 100 | 95 | 91 | 93 | 80 |

Since the potency of FDNP-poly[A] in human serum did not decrease more than 20% in 4 hours at 37° C., the compound can be dissolved in an appropriate solution for parenteral administration.

EXAMPLE 8

Total and Irreversible Inactivation of HIV by FDNP-poly[A] for the Development of Effective Anti-HIV Vaccine The HIV that has been completely and irreversibly inactivated by FDNP-poly[A] (or Y-poly[ A] wherein Y is partially FDNP) is also useful as a complete antigen for the development of an effective anti-AIDS-vaccine.

The world-wide efforts to find an effective vaccine to prevent AIDS have so far been unsuccessful. Vaccines developed with genetically engineered pieces of the AIDS virus do not provide sufficient protection against AIDS mainly because of the extremely high mutation rate of the virus. Recently, encouraging protective effects of a live attenuated HIV vaccine with a deletion in the nef gene has been reported [Daniel, et al., *Science* 258, 1938 (1992)]. This new discovery reminded many researchers of the old practice of using a weakened version of the entire virus to trigger the protective immune response. For example, the live virus can be weakened by treatment with formaldehyde and the weakened virus can then be used as the antigen to trigger immune response. But this is a dangerous procedure because the formation of Schiff base between aldehyde and amino groups is reversible. A reversal of the condensation reaction would regenerate the fully active virus, which may be fatal to the patient.

Since the inactivation of HIV by Y-poly[A] wherein Y is at least partially FDNP can be 100% effective and irreversible, a truly effective anti-AIDS vaccine is developable for humans by using Y-poly[A] (wherein Y is at least partially FDNP)—inactivated HIV as the antigen and introducing it, e.g., injecting it, into a patient.

EXAMPLE 9

Sterilization of Possible Traces of Live HIV in Stored Transfusion Blood

The possible presence of even a trace of live HIV in donated blood poses a constant threat to people who receive blood transfusions as well as to people who administer blood transfusions. Very small but adequate amount of Y-poly[A] (wherein Y is at least partially FDNP) can be added to donated blood before storage in blood banks. Since for irreversible inhibitors $IC_{50}$ decreases with time [Kang and Wang, J. Biol. Chem., in press, May 1994], the added Y-poly[A] inactivates traces of HIV that might be present during storage when used as a safety measure.

In order to test the effectiveness of Y-poly[A], HIV RT (57 nM) was incubated with different concentrations of the inhibitor (FDNP-poly[A](h-$M_r$) for 10 minutes at 25° C. The percentages of initial enzyme activity left after the incubations are listed below:

| Inhibitor concentration (nM) | Enzyme activity (%) |
|---|---|
| 0 | 100 |
| 1.6 | 89 |
| 4.8 | 72 |
| 16.7 | 54 |
| 25 | 42 |
| 33 | 29 |
| 42 | 15 |
| 50 | 6 |
| 55 | 2 |
| 60 | 0 |

EXAMPLE 10

Irreversible Inhibition of Ribonuclease of FDNP-poly[A]

In the biotechnology industry and related research laboratories it is often necessary to isolate large pieces of undamaged RNA. In order to avoid incidental cleavage of the RNA product by traces of exogenous ribonuclease, it is often necessary to preboil all the solution with diethyl pyrocarbonate or to add a ribonuclease inhibitor, generally the commercially available RNasin (obtainable from Promega). Both are expensive procedures for large-scale operation. We discovered that Y-poly[A] (wherein Y is at least partially FDNP) is a potent irreversible inhibitor of ribonuclease. The addition of a small but adequate amount of such Y-poly[A] irreversibly inactivates any trace amount of ribonuclease which might be present in the solutions and containers used in the process. The effectiveness of such Y-poly[A] as a potent inhibitor of ribonuclease is shown by the following experiment.

The catalytic activity of ribonuclease A (RNase A) was determined by monitoring the decrease of absorbance at 300 nm ($A_{300}$) with time due to the catalyzed hydrolysis of cytidine 2':3'-cyclic monophosphate (cCMP) in solution at 25° C. The assay solution contained 1.9 mM cCMP (Na-salt) in 50 mM acetate buffer (pH 5.0). The control reaction in the absence of FDNP-poly[A] was started by injecting 10 µl of 54.4 µM RNase A stock solution into 2.000 ml of the assay solution, mixing and monitoring the decrease of $A_{300}$ with time. For inhibition studies the RNase was preincubated with various concentrations of FDNP-poly[A](h-$M_r$) for 1.0 min, and then injected into the cCMP solution to start the assay. The results are summarized below. The total final concentration of RNase was kept constant at 268 nM, the inhibitor concentration at 54 µM.

| Total preincubation concentration of FDNP-poly[A] (µM) | 0 | 0.5 | 0.8 | 1.3 | 1.7 | 2.3 |
|---|---|---|---|---|---|---|
| % initial RNase activity remaining at 1 minute after mixing | 100 | 89 | 73 | 48 | 25 | 0 |

These data show that even at submicromolar concentrations each FDNP-poly[A] molecule can rapidly inactivate many molecules of exogenous RNase.

EXAMPLE 11

Effectiveness of Double Helical DNP-Poly A-Poly[dT]

Double helical DNP-poly A-poly[dT] has been found to be a more potent inhibitor of HIV-1 RT than is DNP-poly A. The double helical DNP-poly[A]-poly[dT] was formulated by mixing the two components and heating for 5 minutes at 90° C.

The data listed in the following table were obtained by using poly C-$[dG]_{12-18}$ as the template-promoter and $[^3H]$ TTP as the substrate of HIV-1 RT.

| Inhibitor concentration | 5 nM | 10 nM | 20 nM |
|---|---|---|---|
| % inhibition by DNP-poly[A] | 44 | 81 | 94 |
| % inhibition by DNP-poly[A]-poly[dT] | 93 | 98 | 100 |

Clearly the double helical DNP-poly[A]-poly[dT] is a much better inhibitor of HIV-1 RT than is the single-stranded DNP-poly [A].

EXAMPLE 12

Spontaneous Transport of DNP-poly[A] into Human Cells

A 100-µl sample of human adult lymphocytes ($2\times10^6$ cells) was mixed with 100 µl RPMI (Roswell Park Memorial Institute) culture medium and 60 µl of DNP[$^{14}$C]poly[A] (1.3 mg/ml, with specific radioactivity of 120 cpm/pmole). The mixture was incubated at 37° C. and 50 µl aliquots were taken out at certain time intervals, filtered, washed and assayed for radioactivity. Each aliquot was spotted on a piece of membrane filter (FA 1.0 µm, Millipore), suction-filtered and washed 8 times with aqueous 100 mM KCl solution. Each dried filter with cells was assayed for radioactivity by a liquid scintillation counting system. The data from a typical experiment are summarized below.

| Incubation time (h) | 0.1 | 0.5 | 3 | 24 | 48 |
|---|---|---|---|---|---|
| Counts per | 800 | 900 | 1300 | 1800 | 2200 |

| Incubation time (h) | 0.1 | 0.5 | 3 | 24 | 48 |
|---|---|---|---|---|---|
| min (cpm) | | | | | |

These data show that by either diffusion or endocytosis the hydrophobic DNP[$^{14}$C]poly[A] can be spontaneously transported into human adult lymphocytes. Under the same conditions [$^{14}$C]poly[A] did not get into these lymphocytes at all.

EXAMPLE 13

Spontaneous Transport of DNP-poly[A] into Murine Leukemia Virus

Murine Moloney leukemia virus and DNP-poly[A] were used in a model experiment for demonstrating the spontaneous transport of the inhibitor into a retrovirus. In each experiment, 5 μl of the virus suspension was incubated on ice with 37.5 nM DNP-poly[A]. After a certain time, the mixture was centrifuged for 10 min at 100,000 g. The supernatant was carefully removed and the pellet (practically invisible) was washed with 200 μl Tris buffer (50 nM Tris-HCl, pH 7.8). The pellet was then homogenized in the assay buffer (50 mM Tris-HCl, pH 7.8, 60 mM KCl, 2 mM DTT and 0.6 mM Mn-acetate) and incubated with 0.02 U poly[A]-oligo[dT], 1.5 mM[$^3$H]dTTP and 0.1% Triton-100 for 60 min at 37° C. The reaction was stopped with 10% TCA and the catalytic activity (A) of the reverse transcriptase was calculated from the cpm of the precipitated radioactive product [$^3$H]poly[dT]. The experimental data is summarized in the following table where A° represent the initial catalytic activity before incubation with the inhibitor.

| Incubation time (h) | 0 | 0.16 | 0.5 | 1.0 | 24 | 48 |
|---|---|---|---|---|---|---|
| A/A° | 1 | 0.54 | 0.50 | 0.45 | 0.25 | 0.16 |

These data show that DNP-poly[A] can penetrate the envelop of murine leukemia virus and inhibit the reverse transcriptase inside. They indicate that FDNP-poly[A] can also penetrate the envelop of HIV and produce a permanently inactivated HIV suitable for use as an ideal antigen for an anti-AIDS vaccine. Under these same conditions [$^3$H]poly[dT] did not get into the virus at all.

Industrial Applicability

The present invention provides a composition of matter which is useful in the treatment of RNA-virus caused diseases such as AIDS, and in the sterilization of HIV in stored transfusion blood, and which can provide vaccines against RNA-virus caused diseases.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A composition of matter comprising Y-poly[A] representable by the formula:

$$M_n(Y)_m X_{i[A]n}$$

where:

[A]n=polyadenylic acid (5') with n adenylic acid residues, n being at least about 20, Y=FDNP, DNP or partially FDNP and partially DNP, FDNP=3-fluoro-4,6-dinitrophenyl groups, attached covalently to m of the n 2'-OH groups of [A]$_n$ via ether linkage, DNP=2,4-dinitrophenyl groups, attached covalently to m of the n 2'-OH groups of [A]$_n$ via ether linkage, X=an acyl group, i=0 or 1, M=a cation selected to provide a desired degree of solubility for the composition, and has one of the generic structures:

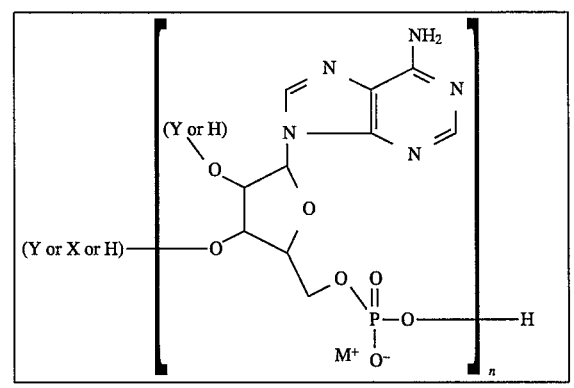

or

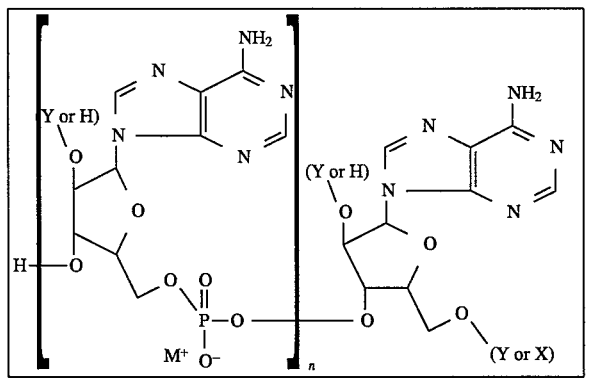

and having a ratio of Y groups to adenine units of at least about 1:5 and wherein n is sufficiently large so that the Y-poly[A] can substantially completely fill the active site cleft of an RNA-virus RT to effectively inactivate reverse transcriptase and/or can effectively inactivate ribonuclease.

2. A composition of matter as set forth in claim 1, wherein Y is partially or all FDNP.

3. A composition of matter as set forth in claim 1, wherein Y is partially or all DNP.

4. A composition of matter as set forth in claim 1, wherein n is at least about 25.

5. A method of treating a mammal having a disease caused by an RNA-virus comprising the administration to the mammal of an effective treatment amount of Y-poly[A].

6. A method as set forth in claim 5, wherein the administering comprises parenteral injection of a sterile injectable formulation containing the Y-poly[A].

7. A method as set forth in claim 5, wherein the administration comprises the oral administration of Y-poly[A].

8. A method as set forth in claim 5, wherein the RNA-virus is HIV and the disease is acquired immuno-deficiency syndrome (AIDS).

9. A method as set forth in claim 5, wherein the RNA-virus is HIV, HTLV, HAV, HCV, influenza-viruses, parainfluenza viruses, RSV, coronavirus or rhinovirus, measles virus or mumps virus and the disease is, respectively, acquired immuno-deficiency syndrome (AIDS), adult T-cell leukemia/lymphoma, hepatitis A, hepatitis C., influenza, parainfluenza, infant bronchiolitis and infant pneumonia, common cold, measles or mumps.

10. A method as set forth in claim 5, wherein Y is partially or all FDNP.

11. A method as set forth in claim 5, wherein Y is partially or all DNP.

12. A method of temporarily protecting a healthy mammal from an RNA-virus infection comprising administering to the mammal an effective preventative amount of Y-poly[A] as defined in claim 1.

13. A method as set forth in claim 12, wherein the administering comprises parenteral injection of a sterile injectable formulation containing the Y-poly[A].

14. A method as set forth in claim 12, wherein the administration comprises the oral administration of Y-poly[A].

15. A method as set forth in claim 12, wherein the RNA-virus is HIV and the disease is acquired immuno-deficiency syndrome (AIDS).

16. A method as set forth in claim 12, wherein the RNA-virus is HIV, HTLV, HAV, HCV, influenza-viruses, parainfluenza viruses, RSV, coronavirus or rhinovirus, measles virus or mumps virus and the disease is, respectively, acquired immuno-deficiency syndrome (AIDS), adult T-cell leukemia/lymphoma, hepatitis A, hepatitis C., influenza, parainfluenza, infant bronchiolitis and infant pneumonia, common cold, measles or mumps.

17. A method as set forth in claim 12, wherein Y is partially or all FDNP.

18. A method as set forth in claim 12, wherein Y is partially or all DNP.

* * * * *